US006325538B1

(12) United States Patent
Heesch

(10) Patent No.: US 6,325,538 B1
(45) Date of Patent: Dec. 4, 2001

(54) RADIATION FIELD ISOLATOR APPARATUS

(76) Inventor: Christian M. Heesch, #1 Stones Throw Dr., Houma, LA (US) 70364

( * ) Notice: Subject to any disclaimer, the term of this patent is extended or adjusted under 35 U.S.C. 154(b) by 0 days.

(21) Appl. No.: 09/528,039

(22) Filed: Mar. 17, 2000

(51) Int. Cl.⁷ .................................................. G21K 1/00
(52) U.S. Cl. .................. 378/203; 250/515.1; 250/517.1; 250/519.1; 128/846
(58) Field of Search ............................ 378/203; 128/846, 128/849, 857, 853; 250/515.1–516.1, 517.1–518.1, 519.1

(56) References Cited

U.S. PATENT DOCUMENTS

| | | | |
|---|---|---|---|
| 3,737,661 | * 6/1973 | Applegate | 378/203 |
| 3,967,129 | * 6/1976 | Winkler | 250/519.1 |
| 4,062,518 | * 12/1977 | Stivender et al. | 250/519.1 |
| 4,581,538 | * 4/1986 | Lenhart | 250/519.1 |
| 4,852,141 | * 7/1989 | Horn | 378/203 |
| 4,977,585 | * 12/1990 | Boyd | 378/4 |
| 5,523,578 | * 6/1996 | Herskovic | 378/65 |
| 5,533,089 | * 7/1996 | Mulhern | 378/150 |
| 5,937,028 | * 8/1999 | Tybinkowski et al. | 378/203 |

\* cited by examiner

Primary Examiner—Drew Dunn
(74) Attorney, Agent, or Firm—Garvey, Smith, Nehrbass & Doody, L.L.C.

(57) ABSTRACT

A shield apparatus is disclosed that encloses the human torso (or part of a human torso) during X-ray procedures. The shield protects medical personnel from scatter radiation, is adjustable to fit different size torsos, and will move with the X-ray equipment as the position of the equipment is adjusted to examine different areas of the body.

27 Claims, 14 Drawing Sheets

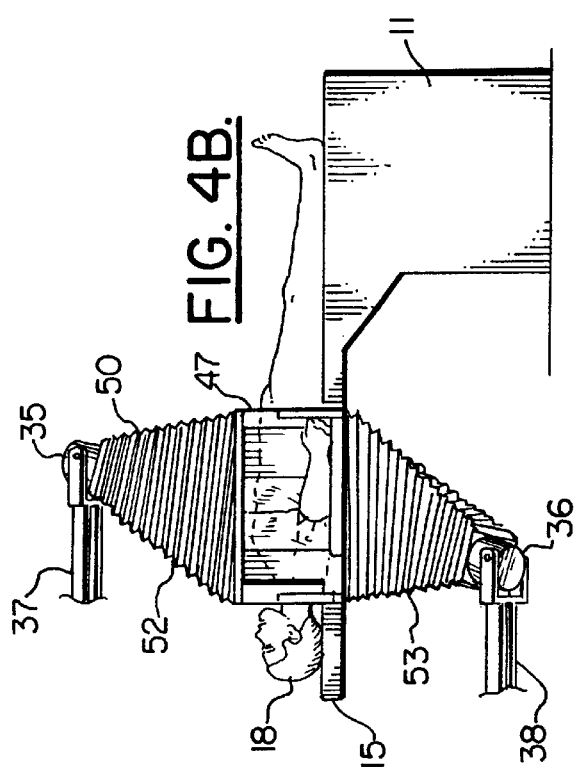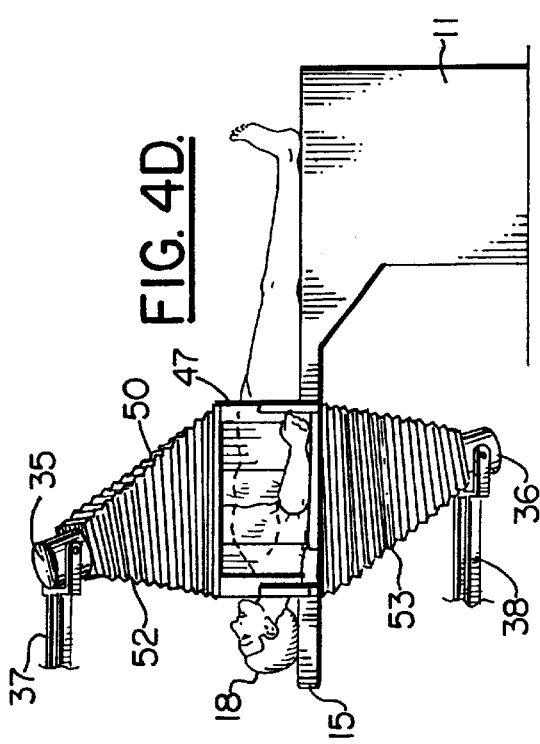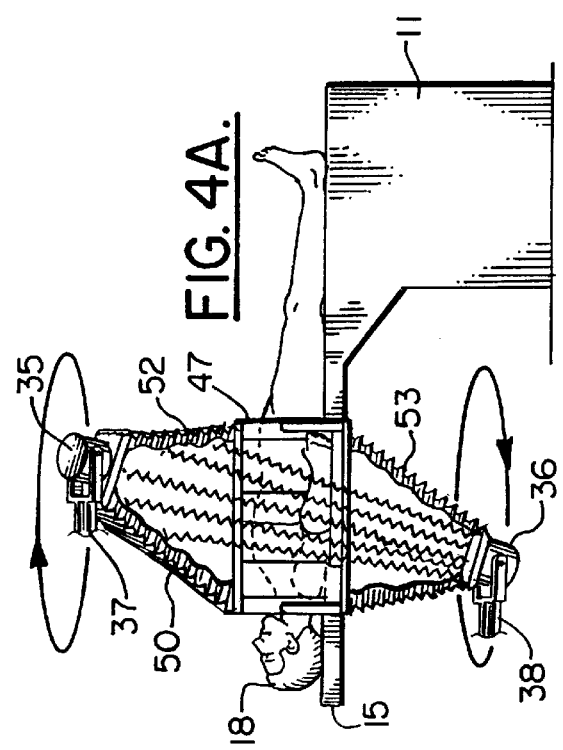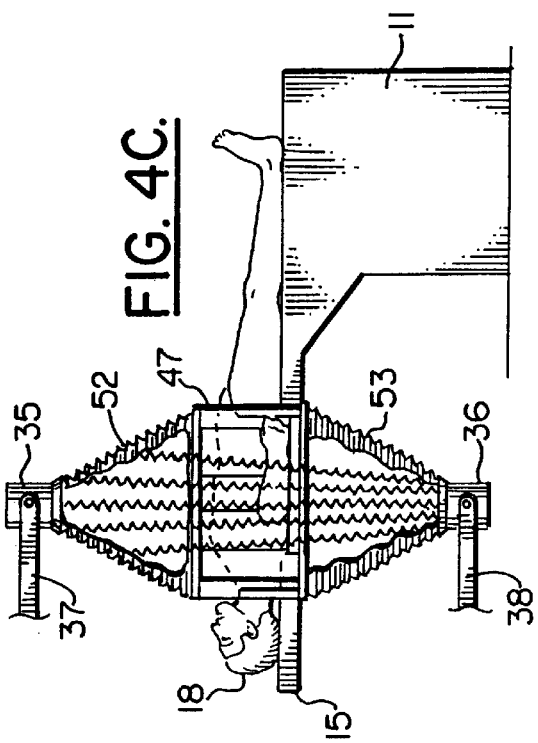

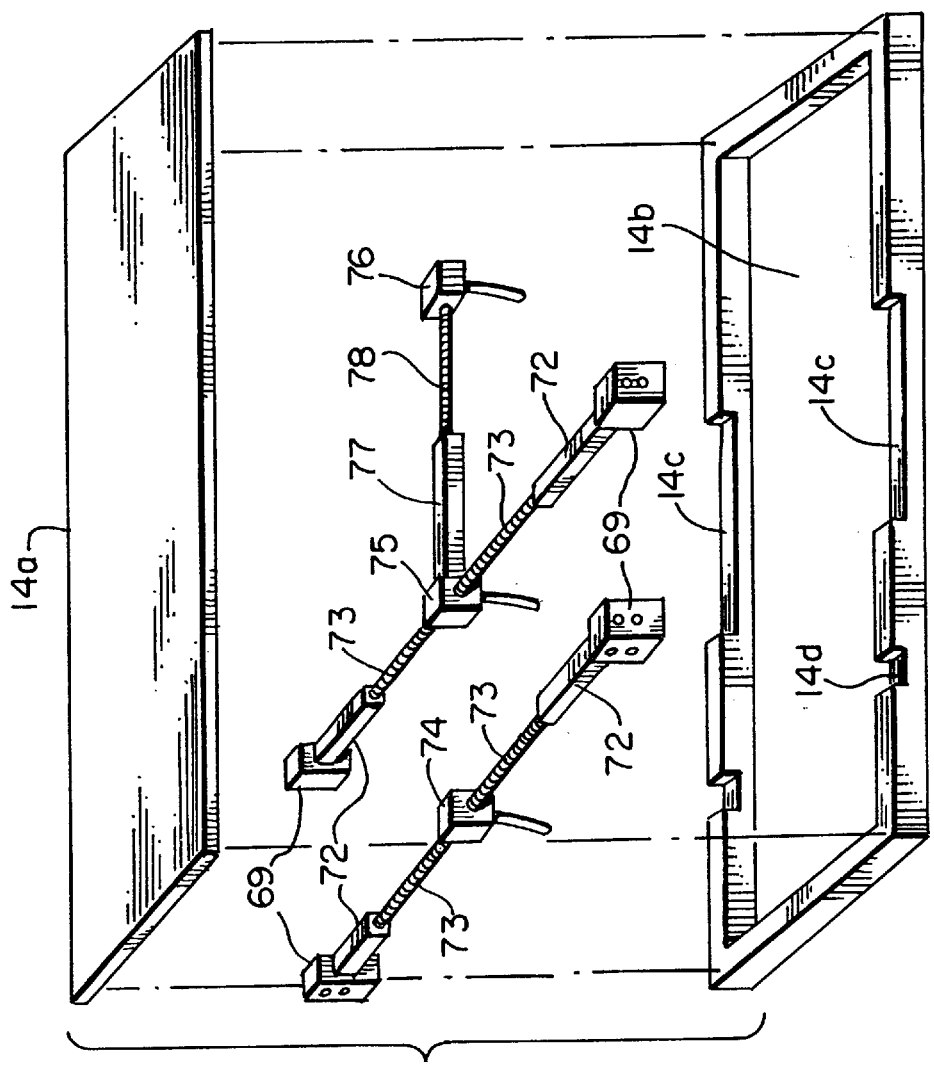

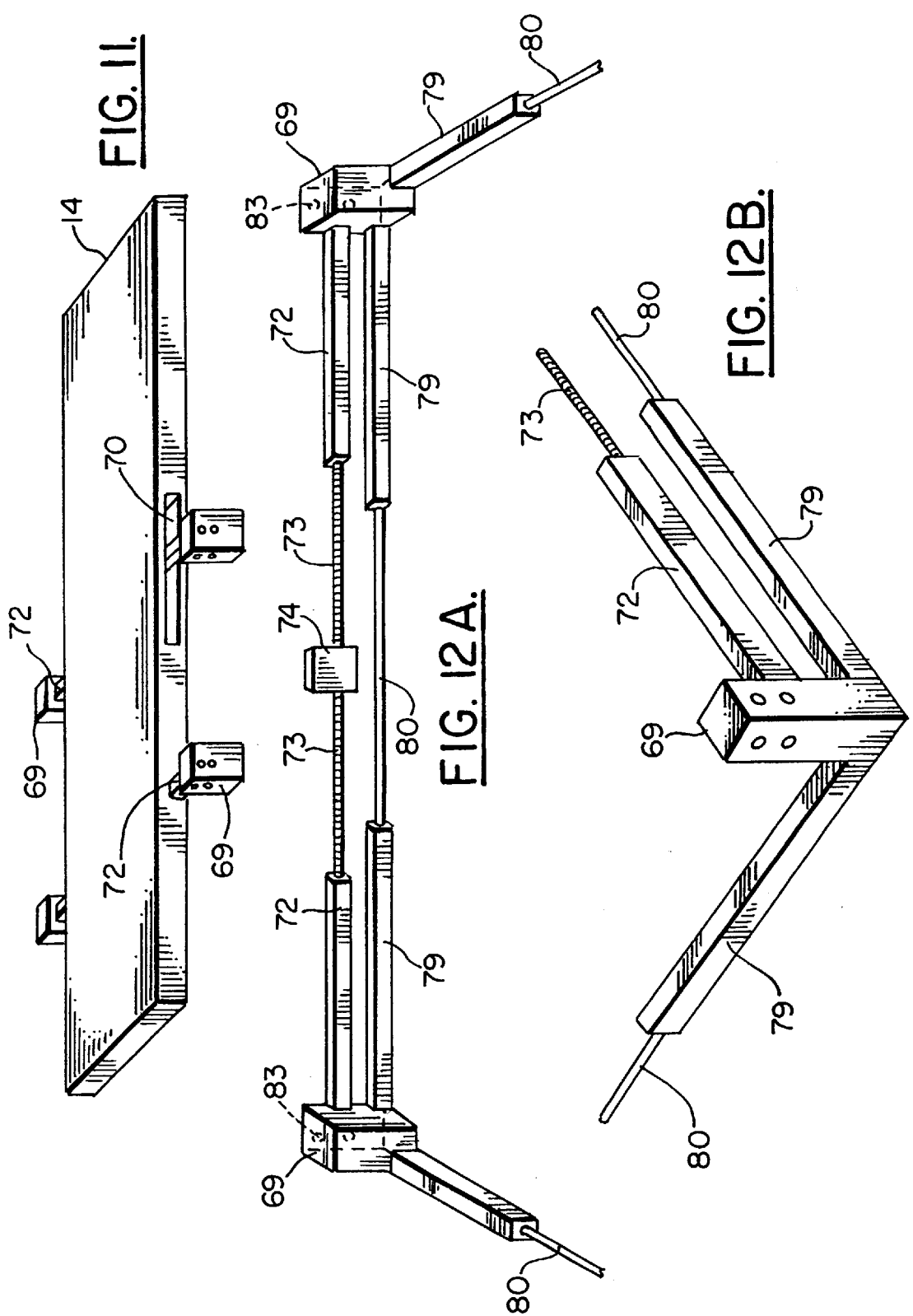

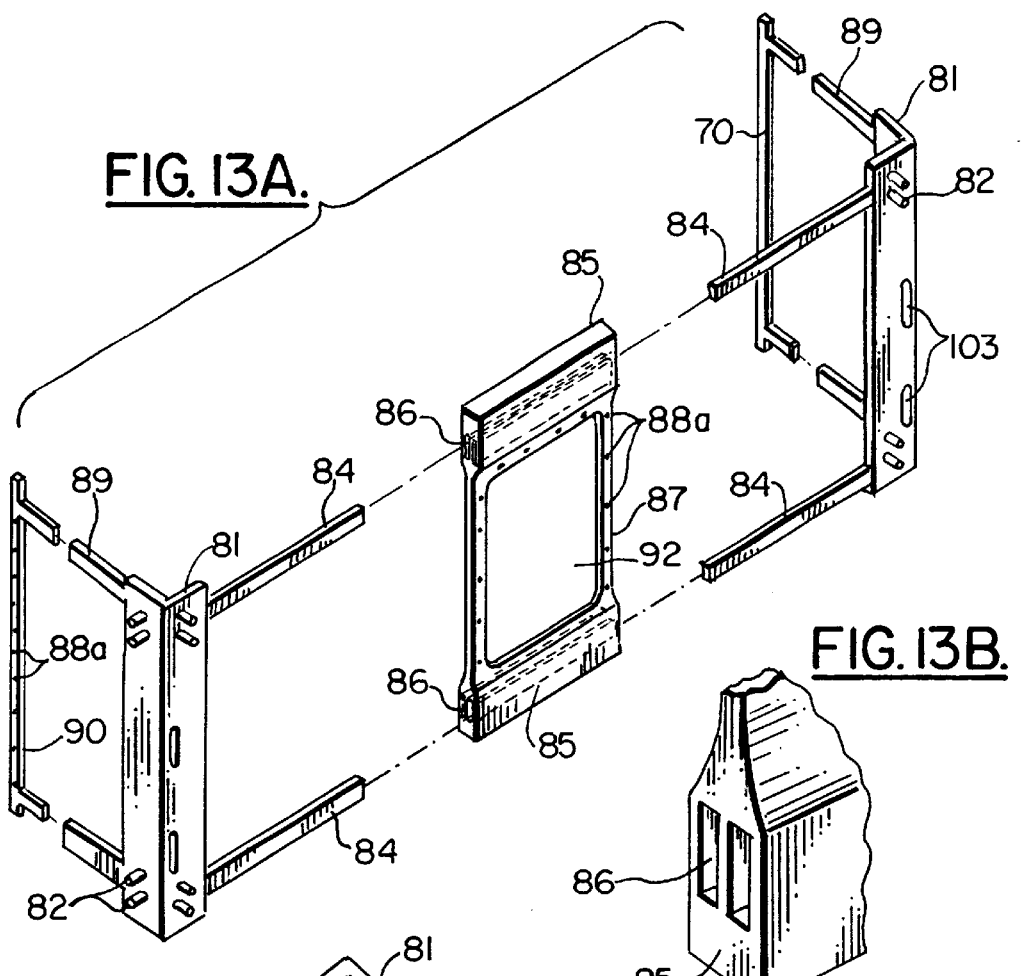
FIG. 13A.
FIG. 13B.
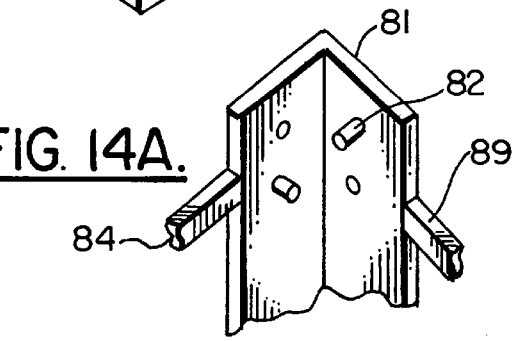
FIG. 14A.
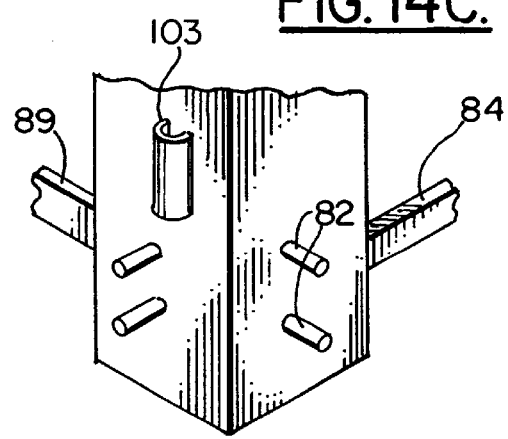
FIG. 14B.
FIG. 14C.

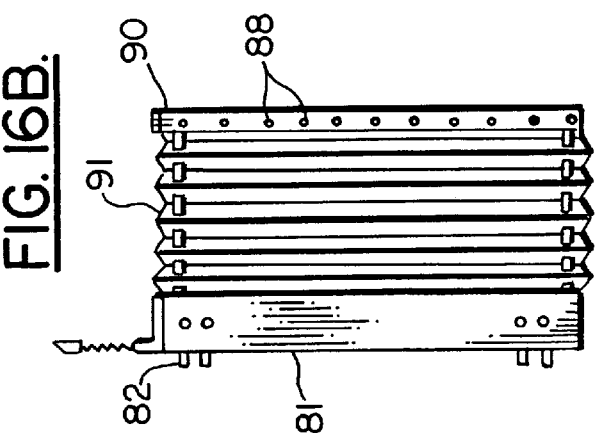
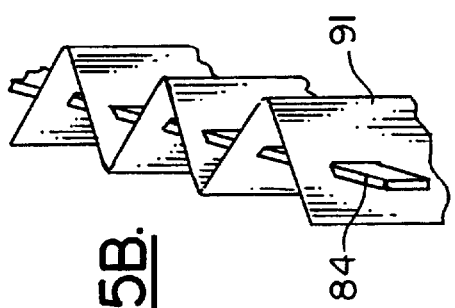
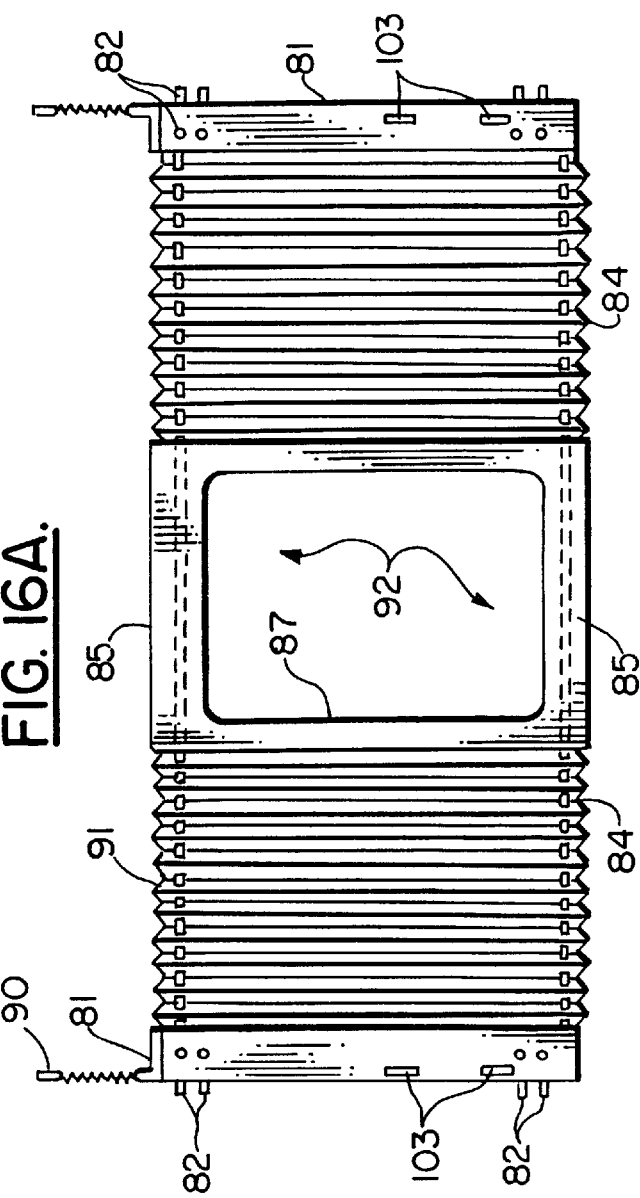

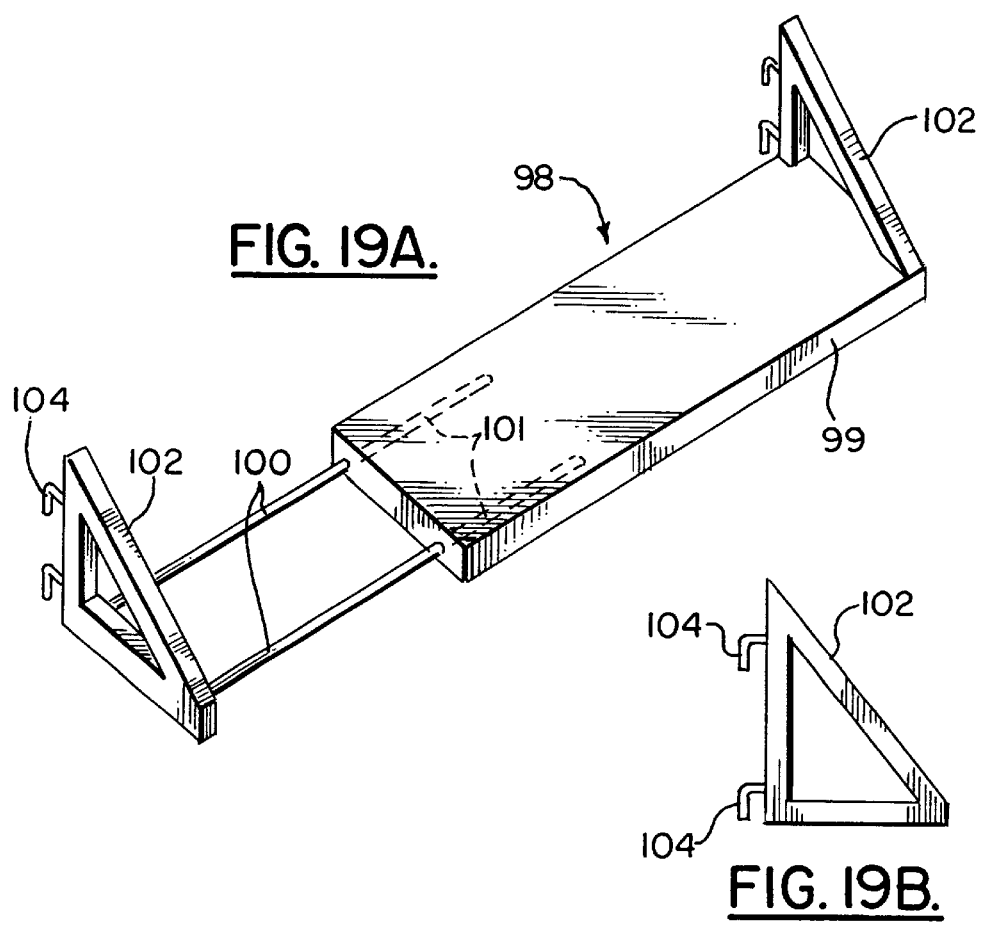
FIG. 19A.
FIG. 19B.
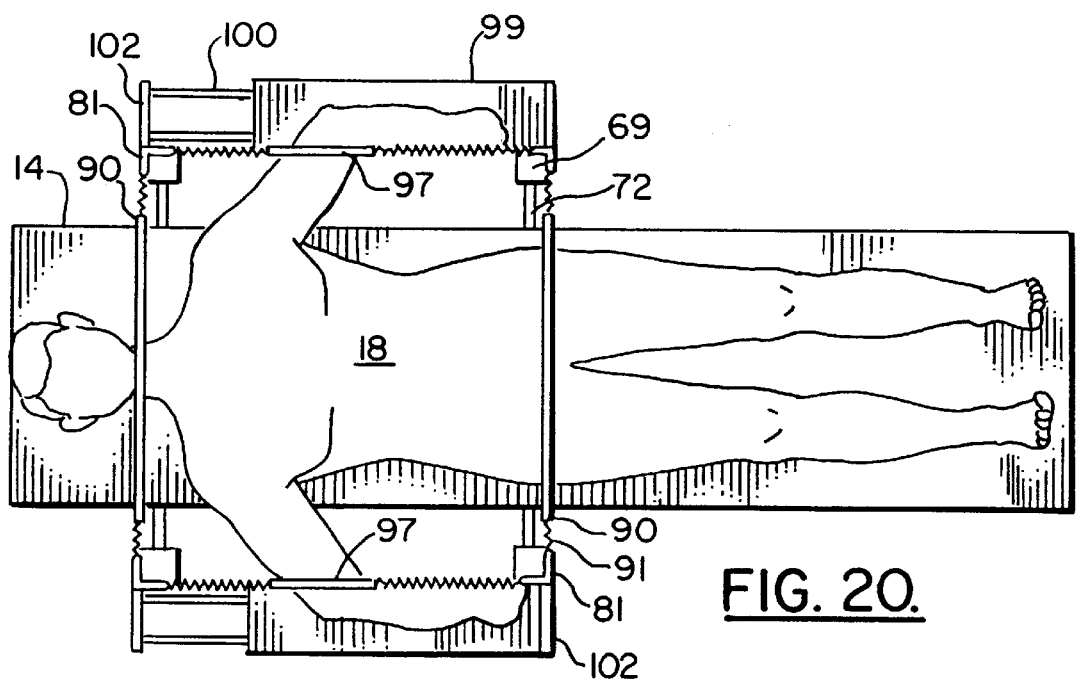
FIG. 20.

RADIATION FIELD ISOLATOR APPARATUS

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates, in general, to radiation shields, and, in particular, to an improved radiation shield for the protection of medical personnel and patients during x-ray guided medical procedures. Some commercially available shields include leaded aprons or drapes placed over a portion of the patient's body that is to be protected.

The present invention relates specifically to the field of cardiac catheterization and intervention. Currently, ceiling mounted movable lead glass shields are used to protect the chest of the physician. In addition, each member of the catheterization team is obliged to wear protective lead vests, skirts, or coats. These protective measures are inadequate for several reasons:

1. Protective lead aprons and coats are heavy and very uncomfortable. Over hours, they lead to operator fatigue and back pain. Over years, they may lead to chronic degenerative back problems.

2. Protective aprons, coats, and mobile ceiling mounted shields offer incomplete protection. The operators head, hands, arms, and lower legs are freely exposed to radiation. Especially problematic is the lack of protection of the long bones of the arms and legs, since radiation exposure of hematopoetic stem cells in the bone marrow may lead to the development of leukemia.

3. The patient, while only temporarily exposed, is completely lacking protection. Especially radiation sensitive areas, exposed with traditional radiation equipment, are thyroid gland, eyes, the long bones of arms and legs, and gonadal tissues.

2. General Background of the Invention

Scatter radiation is that radiation that is deflected away from a selected x-ray field by media it encounters. This scatter radiation poses health hazards, most notably the risk of cancer, leukemia, and cataract formation in the eye. Patients, while directly exposed to the X-ray beam, are currently felt to be only at moderate risk because the time of exposure is limited. On the other hand, physicians and allied health personnel assisting in the catheterization laboratory are repeatedly exposed to cumulative scatter radiation in doses inverse to the distance from the source.

Currently, ceiling mounted movable lead glass shields are used to protect the chest of the physician. In addition, each member of the catheterization team is obliged to wear protective lead vests, skirts, or coats. These protective measures are inadequate for several reasons: Protective lead aprons and coats are heavy and very uncomfortable. Over hours, they lead to operator fatigue and back pain. Over years, they may lead to chronic degenerative back problems. Protective aprons, coats, and mobile ceiling mounted shields offer incomplete protection. The operators head, hands, arms, and lower legs are freely exposed to radiation. Especially problematic is the lack of protection of the long bones of the arms and legs, since radiation exposure of hematopoetic stem cells in the bone marrow may lead to the development of leukemia. The patient, while only temporarily exposed, is completely lacking protection. Especially radiation sensitive areas, exposed with traditional radiation equipment, are thyroid gland, eyes, the long bones of arms and legs, and gonadal tissues.

A new type of radiation shield is proposed by the present invention. This shield would almost completely isolate the trajectory between a radiation generator and a camera. Radiation scatter would be almost absent, allowing for the complete elimination of the personal radiation protection of the operators. Radiation to the eyes, thyroid gland, long bones of the legs and arms, and the gonads of the patient would be greatly reduced. This device could serve not only for cardiac catheterization, but for a variety of radiological procedures.

In the prior art, various shields devices for use with X-rays have been proposed. For example, U.S. Pat. No. 2,526,390 to Moran et al. discloses an X-ray apparatus for industrial use which is automatically energized only when the operator is shielded from stray X-rays.

An early patent that is directed to an x-ray shield is the Shasky U.S. Pat. No. 2,794,128 entitled "X-Ray Shield". In the Shasky patent, the x-ray machine has a mounting plate with a plurality of clips attached thereto at one edge thereof. A shield of flexible opaque radiant material is affixed to the clips.

The Winkler U.S. Pat. No. 3,967,129 discloses a radiation shield in the form of a stranded curtain made up of bead-chains whose material and geometry are selected to produce a cross-sectional density that is the equivalent of 0.25 mm or more of lead and which curtain may be mounted on various radiological devices to shield against scattered radiation while offering a minimum of obstruction to the radiologist.

U.S. Pat. No. 3,984,696 issued to Collica discloses a radiation guard suitable for use in conjunction with a diagnostic table and penetrable by the hands of an operator to facilitate moving or examining a patient positioned on a table. In accordance with the invention there is provided a supportive mountable at about an edge of the table so as to extend vertically from about the edge, the frame comprising at least a pair of spaced bars. A plurality of strips of flexible radiation shielding material are mounted across the bars in closely spaced relationship, the strips being mounted sufficiently close together to prevent substantial radiation leakage through the frame. The hands of an operator can be inserted between the adjacent strips to manually reposition or examine a patient while protecting most of the operator's body from substantial radiation.

U.S. Pat. No. 4,062,518 issued to Stivender discloses a diagnostic x-ray table having a first group of x-ray shielding panels that are supported for rotation on a carrier and another group of panels that are supported on a lever that is pivotally connected to the carrier. The lever may be aligned with the carrier to present the combined width of all panels across the front of a combination spot film and fluoroscopic device. Means responsive to pivoting the lever along the side of the apparatus rotate the first group of panels to substantial parallelism with the second group to present the panels along the side of the apparatus when the spot film and fluoroscope device is angulated to put the patient being examined in an erect posture.

U.S. Pat. No. 3,737,661 to Applegate discloses a shielded X-ray device for a portable X-ray apparatus comprising a collimator and a rotatably and pivotally mounted container which encloses a portion of an object to be X-rayed.

U.S. Pat. No. 4,157,476 to O'Connor discloses a dental X-ray apparatus in which the X-ray tube is mounted in a casing which shields against stray radiation being projected through the housing of the tube head.

U.S. Pat. No. 4,286,169 to Rossem discloses a shield for radio-isotope producing generators which includes a movable portion which can be moved with respect to a stationary portion. When in the open position, the generator can be inserted into the device, and when in the closed position, the generator is shielded.

A radiation shield is disclosed in the Lenhart U.S. Pat. No. 4,581,538. The '538 patent discloses a shield for protecting a person from radiation being used to irradiate a work area, while permitting the person to observe and to have access to the work area, including a radiation-shielding observation window, and a flexible, mechanically penetrable radiation-shielding curtain adjacent the window. Another Lenhart U.S. Pat. No. 5,006,718 discloses an x-ray shield that comprises an elongated mounting bar having a linear main section and linear hinge section hingedly connected together, a mounting bracket on one side of the linear main section adapted for connection to the accessory rod on the side of an x-ray examination table and draped opaque to x-ray extending from the mounting bar to the floor to protect personnel from x-ray radiation emanating from below the examination table.

U.S. Pat. No. 5,090,044 issued to Kobayashi discloses an apparatus for performing an x-ray examination wherein a catheter is inserted into a blood vessel of a subject from the brachial region, an x-ray shield is mounted on an arm rest to shield scattered x-rays passed from the subject, to thereby protect operator's hands handling the catheter.

U.S. Pat. No. 5,194,742 issued to Avnery discloses a novel technique and apparatus for shielding electron beam and similar product irradiation zones with a separable shielding housing extending transversely of the longitudinal line of product flow and slidably openable in a transverse direction orthogonal to both the electron beam and the direction of product flow, both in passing the beam and along the line, resulting in substantial space saving, more facile accelerating to the irradiation and product feed zone and less costly and sizeable shielding apparatus.

The Kornfeldt et al. U.S. Pat. No. 5,483,562 discloses a device for volume delimitation during work with contaminated parts.

A radiation shield is the subject of the Mussman U.S. Pat. No. 5,883,394.

U.S. Pat. No. 5,604,784 to Widlicka et al. discloses the use of granulated bismuth mixed with a liquid carrier that can be applied to a surface to provide radiation attenuation for shielding purposes.

U.S. Pat. No. 4,852,141 to Horn discloses a shielding apparatus for use with an X-ray generator which has a shielding cone extending from the generator to reduce the emission of stray X-rays.

The Huttner U.S. Pat. No. 5,892,238 discloses a radiation therapy shielding assembly. The shielding assembly includes a pair of shielding sections. The shielding sections defme a cavity for receiving a patient. Each of the shielding sections define a predetermined edge surface. The predetermined edge surfaces of the pair of shielding sections are spaced from one another to define a patient treatment area.

None of the prior art known to applicant addresses the need for a shielding device which can be used for diagnostic and therapeutic X-ray procedures in humans, and which can be easily and quickly adjusted to cover substantially the entire human torso while adjusting to different sizes of torsos, and which can be easily and quickly adjusted to different camera and radiation generator positions.

BRIEF SUMMARY OF THE INVENTION

A new type of radiation shield is proposed by the present invention. This shield would almost completely isolate the trajectory between the radiation generator and the camera. Radiation scatter would be almost absent, allowing for the complete elimination of the personal radiation protection of the operators. Radiation to the eyes, thyroid gland, long bones of the legs and arms, and the gonads of the patient would be greatly reduced. This device could serve not only for cardiac catheterization, but for a variety of radiological procedures.

The present invention provides an improved x-ray and shield apparatus that includes an x-ray generation device and a camera that are supported in spaced apart positions on a superstructure. The superstructure is in the nature of an adjustable frame mounted to a base. A table has an upper surface for supporting a patient, the table being supported by a suitable base or frame.

A shield apparatus is provided that includes one or two spaced apart tapered sections, each being constructed in the nature of a bellows, and a central, rectangular housing. The rectangular housing is fitted to the table and provides openings that accommodate a patient's head, arms, and lower torso.

The superstructure can include a pair of inclined beams that have upper and lower end portions, the upper end portions supporting an upper arm, the lower end portions supporting a lower arm.

Each of the arms preferably provides a yoke that supports either the camera or the x-ray generator. For example, the upper arm can provide a yoke that holds the film. The lower arm preferably provides a yoke that supports the x-ray generator.

The housing can be a rectangular frame comprised of four flat, rectangular side walls that are connected end to end. The upper section can be a tapered accordion or bellows that tapers from a larger cross section that connects to the housing and a smaller cross section that connects to the camera or x-ray generator as selected by the user.

Similarly, the lower section is in the nature of an accordion or bellows having a larger end portion that attaches to the housing and a smaller cross-sectional portion that attaches to the x-ray generator or camera.

The superstructure that supports the camera and generator is preferably adjustable in numerous ways. These can include, for example, a translation of the camera in a proximal to distal direction in relation to the patient's body. The superstructure can also be adjusted laterally relative to the patient's body. The camera and x-ray generator can be rotated with respect to the superstructure to provide a further adjustment.

Because of the accordion-like bellows construction of the upper and lower shield sections, the x-rays that are transmitted through the patient are retained within the shield what adjustments that are made to the position of either the camera or the x-ray generator. Because of the construction of the upper and lower shield sections, the camera and x-ray generator can be adjusted and articulated into many positions relative to the patient and relative to each other.

The present invention is directed to a shield that can be applied to the human torso during X-ray procedures. The shield is adjustable to fit torsos of different size, and will move with the X-ray equipment as the X-ray beam targets different areas of the torso.

It is an object of the present invention to provide a new and improved radiation shield.

It is also an object of the present invention to provide a new and improved radiation shield that is adjustable to different size torsos.

Another object of the present invention is to provide a new and improved radiation shield that can be moved with the radiation equipment as the equipment and the trajectory of the radiation beam are adjusted to image different areas of a person's torso.

It is an object of the present invention to provide a new and improved radiation shield that changes its shape, constantly adjusting to various angulations of the radiation beam. It is an object of the present invention to provide anew and improved radiation shield that will allow medical personnel to substantially reduce or completely omit the wearing of personal X-ray protection devices.

It is furthermore an object of the present invention to provide a new and improved radiation shield that will reduce radiation exposure to those parts of a patient's body which are not within the trajectory of the direct radiation beam.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIGS. 4A–4D are sequential views illustrating the apparatus of the present invention in different positions relative to a patient;

FIGS. 9A and 9B are fragmentary magnified views of the preferred embodiment of the apparatus of the present invention showing the elements connecting the stabilizing rods to the individual segments of the upper and lower shields;

FIG. 10 is an exploded perspective view of the drive unit, and its position in relation to the two segments of the table board in which it is contained;

FIG. 11 is a perspective view of the drive unit, enclosed by the two segments of the table board;

FIGS. 12A and 12B illustrate in detail the connections between the various parts of the drive unit and the frame of the lower shield at its base, using two views of parts of these structures from different angles;

FIGS. 13A and 13B are perspective views of the separated parts forming the frame of the side wing of the middle portion of the shield;

FIGS. 14A–14C consist of several perspective views of portions of the angle struts of the invention's middle portion;

FIGS. 15A–15C consist of several perspective views of the connection between the vertical folding segments of the middle portion and its frame, showing magnified partial views of these segments;

FIGS. 16A and 16B consist of a side view and a top view of the side wing of the invention's middle portion;

FIGS. 17A–7C depict the three types of cuff screens which are part of the middle portion;

FIGS. 19A and 19B illustrate the armboard in a perspective view and a top view;

FIG. 20 is a schematic illustration of the position of this invention in relation to the patient;

DETAILED DESCRIPTION OF THE INVENTION

Figure 1:
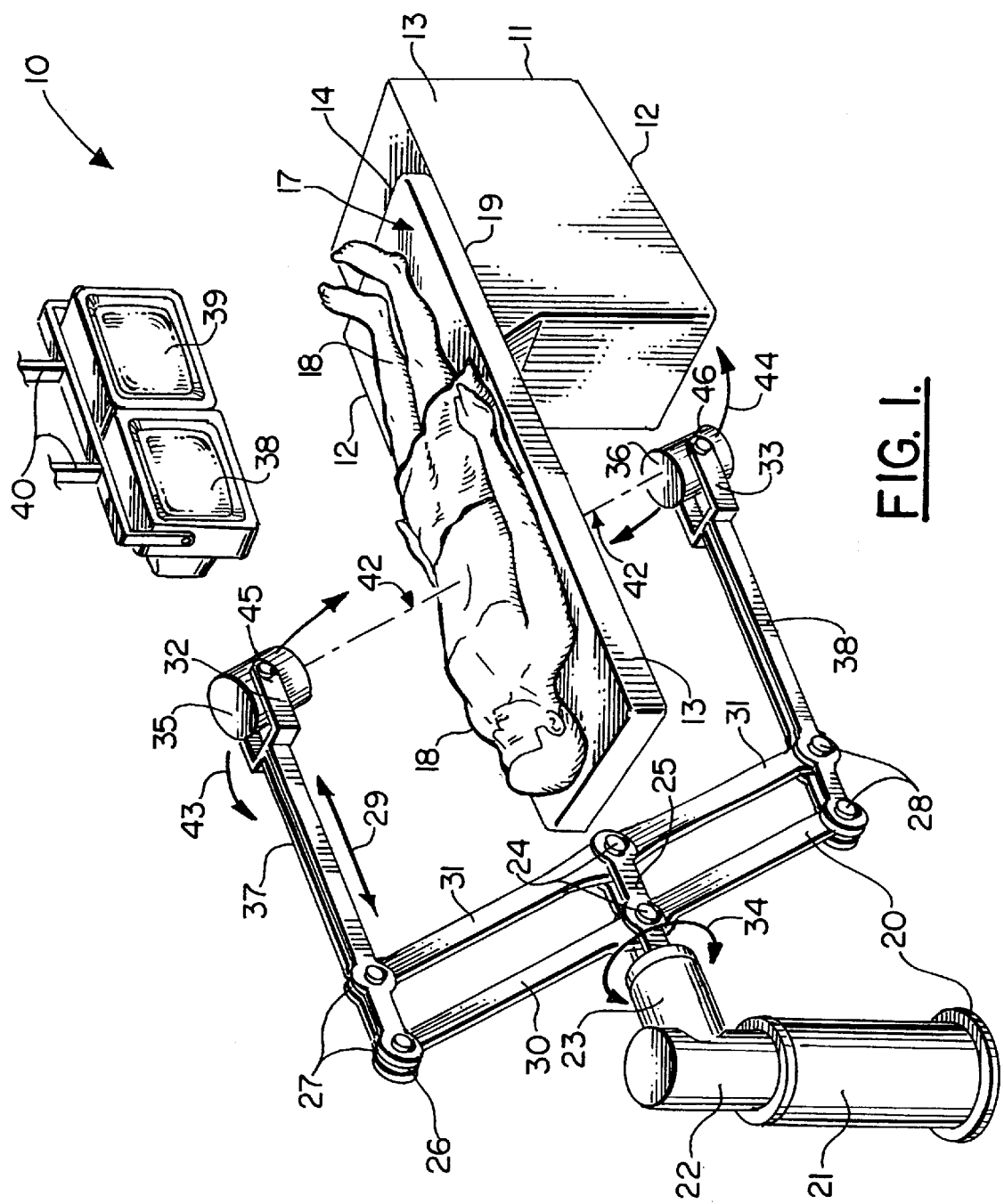
FIG. 1 is a perspective view of the preferred embodiment of the apparatus of the present invention showing the shield portion removed for clarity.
Figure 3:
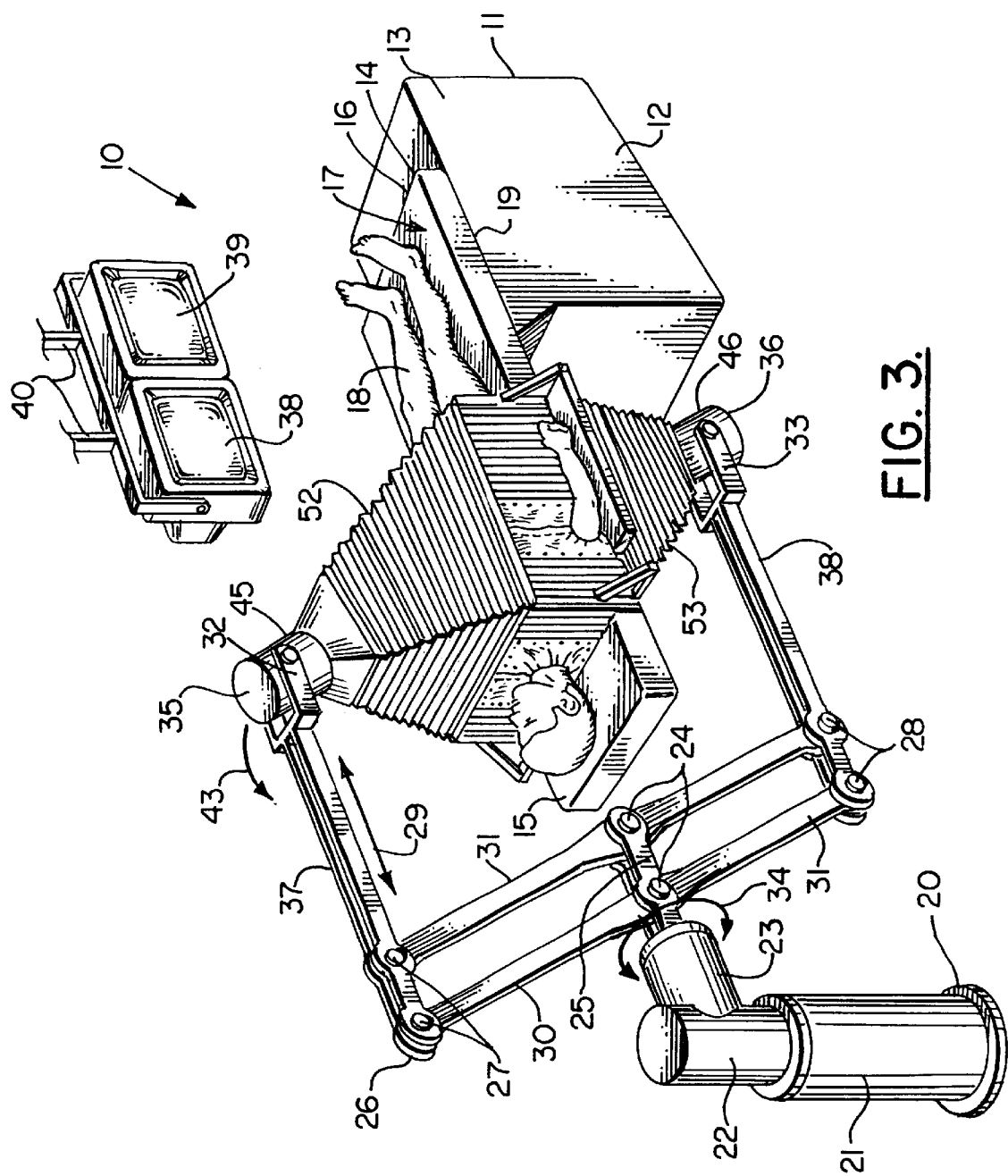
FIG. 3 is a perspective view of the preferred embodiment of the apparatus of the present invention.
Figure 23:
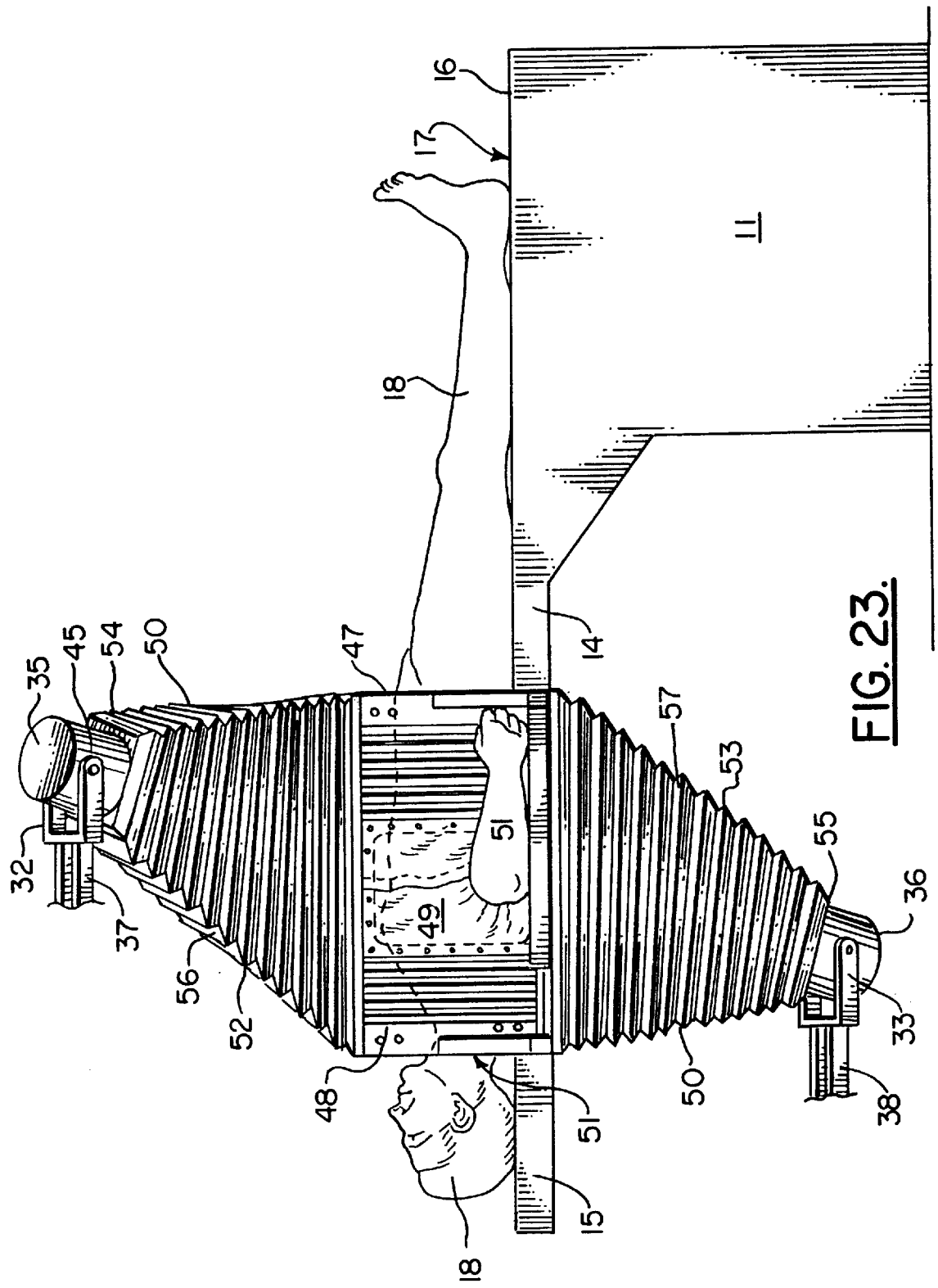
FIG. 23 is a partial side elevational view of the preferred embodiment of the apparatus of the present invention.

FIGS. 1, 3 and 23 show generally the preferred embodiment of the apparatus of the present invention designated generally by the numeral 10. In FIG. 1, the shield is removed for clarity. The apparatus 10 of the present invention provides a shielded x-ray apparatus that includes a frame 11 having a lower end 12 that rests upon a supporting surface such as a floor and an upper end portion 13 that supports a table 14. The table 14 has head and foot end portions 15, 16 respectively and an upper surface 17. The upper surface 17 is receptive of patient 18 as shown. A suitable attachment such as a conventional sliding rail attachment secured by bolting, riveting, welding or the like can be used to form an attachment at 19 between frame 11 and table 14.

An x-ray unit 20 includes a base 21 having a vertical section 22, horizontal section 23 and superstructure 26. The superstructure 26 is attached to vertical section 22 with support beam 25. Arrow 34 indicates that beam 25 can be rotatably supported by horizontal section 23 using a motor drive, for example. Support beam 25 pivotally supports superstructure 26 at connections 24 (pinned, for example). Superstructure 26 is comprised of inclined arms 30, 31 and beams 37, 38 that can be generally horizontally positioned. Pinned connections 27, 28 can be used to join the arms 30, 31 to the beams 37, 38 of superstructure 26. Each of the beams 37, 38 supports a yoke. Beam 37 supports yoke 32. Beam 38 supports yoke 33. The beams 37, 38 are supported by inclined arms 30, 31. Pinned connections 27, 28 can be used to join each of the beams 37, 38 to the respective end portions of inclined arms 30, 31 as shown in FIGS. 1 and 3.

A pair of monitors 39, 40 can be positioned next to table 11 so that a radiologist can view the monitors 39, 40. Monitors 39, 40 are supported by a frame such as monitor support 41 shown in FIGS. 1 and 3. In FIG. 1, reference line 42 indicates the path that x-rays travel when emitted by radiation generator 36 in the direction of camera 35 which contains film. A pinned connection 45 can be used to join camera 35 to upper yoke 32. Similarly, pinned connection 46 can be used to join x-ray generator 36 to lower yoke 33. Arrows 43, 44 in FIGS. 1 and 3 indicate schematically the pivotal movement of camera 35 and x-ray generator 36 respectively relative to superstructure 26. Arrow 29 in FIGS. 1 and 3 schematically indicates the adjustable movement in a fore and aft direction relative to support 25 of arms 30 and 31. In this fashion, the superstructure 26 can be used to move the position of both camera 35 and x-ray generator 36. A telescoping mechanism (not depicted), located either at arms 30, 31 or at camera 35, can be used to vary the distance between camera 35 and the patient 18.

The present invention has particular utility to cardiac catheterization procedures. During cardiac catheterization and intervention, procedures for which the illustrated equipment is typically used, a physician advances catheters into the patient's heart, usually through veins and arteries cannulated in the patients groin or elbow crease. These catheters are then used to inject contrast dye into the patient's cardiac chambers or blood vessels surrounding the heart, and small steerable and/or implantable tools, such as balloons, stents, and rotablators, are used to remove or modify pathologic narrowings of coronary arteries or heart valves.

Figure 2:
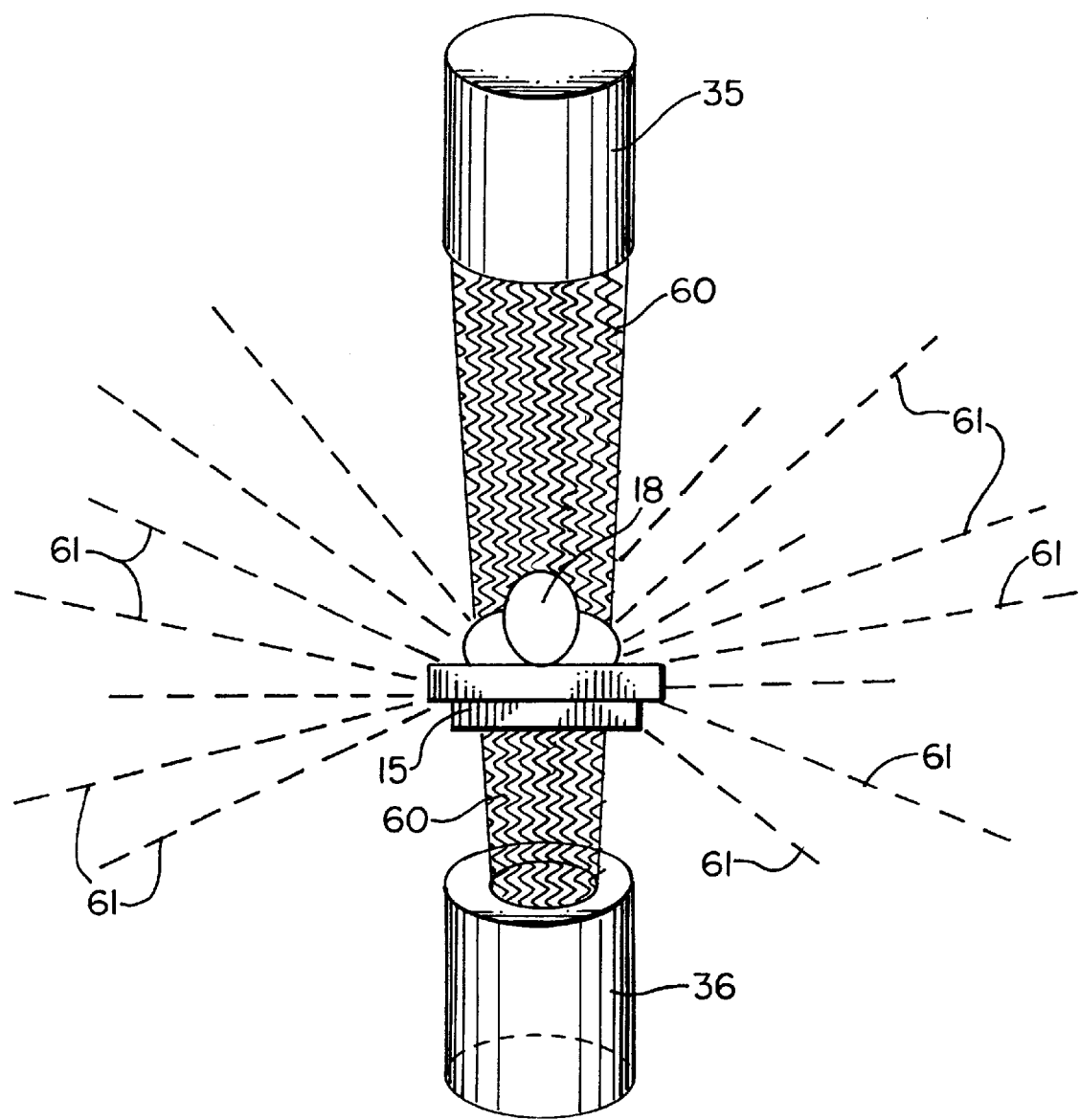
FIG. 2 is a schematic diagram of a typical x-ray unit showing the film, x-ray generator, patient and radiation path.

While most of the radiation beam 60 (see FIG. 2) emitted by the generator 36 crosses the table 14 and the patient 18, and ultimately enters the camera 35, a sizable portion is deflected by the different media it encounters on the way, as shown schematically in FIG. 2, leading to scatter radiation, depicted by dotted lines 61. This scatter radiation 61 poses health hazards, most notably the risk of cancer, leukemia, and cataract formation in the eye. Patients, while directly exposed to the X-ray beam 60, are currently felt to be only at moderate risk because the time of exposure is limited. On the other hand, physicians and allied health personnel assisting in the catheterization laboratory are repeatedly exposed to cumulative scatter radiation in doses inverse to the distance from the source.

This scatter radiation is confined by the shield 50. Shield 50 consists of a rectangular middle portion 47, located between upper shield section 52 (attached to the camera 35) and lower shield section 53 (attached to the radiation generator). Attention is first directed to the upper and lower shield sections. Each of these shield sections (52, 53) has the shape of a truncated pyramid with four lateral walls 56. Each lateral wall consists of two half pieces 58, 59, which in turn are formed by a plurality of horizontal shield segments 57, joined by hinges 62.

Figure 5A:
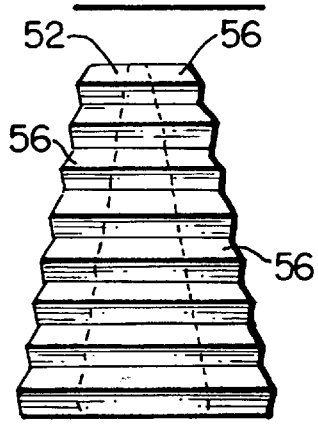
FIGS. 5A–5D is a fragmentary view of the preferred embodiment of the apparatus of the present invention showing a shield section.
Figure 5B:
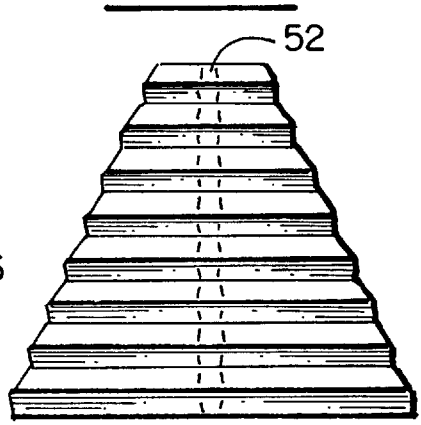
Figure 5C:
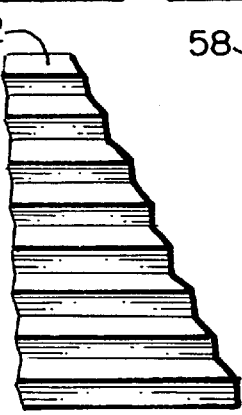
Figure 5D:

FIGS. 5a–5d illustrate this slidable joining of half pieces 58 and 59. FIG. 5c shows a single half piece. The flexible connection of horizontal shield segments 57 through hinges 62 allows for the extension or reduction of the height of the half piece. The two opposing half pieces 58, 59 are connected slidably through projections 64 on half piece 58 which engage matching slots 63 on half piece 59. In so engaging each other, the two opposing halfpieces show a section of overlap 151. This width of this section of overlap 151 will vary, depending on the degree of engagement between the two opposing half pieces 58 and 59. In FIG. 5a, the two half pieces are deeply engaged, forming a large section of overlap 151. In FIG. 5b, the two half pieces are barely joined, forming a small section of overlap 151. This overlapping of the opposing half pieces 58 and 59 is schematically illustrated in FIG. 5d.

Figure 6A:
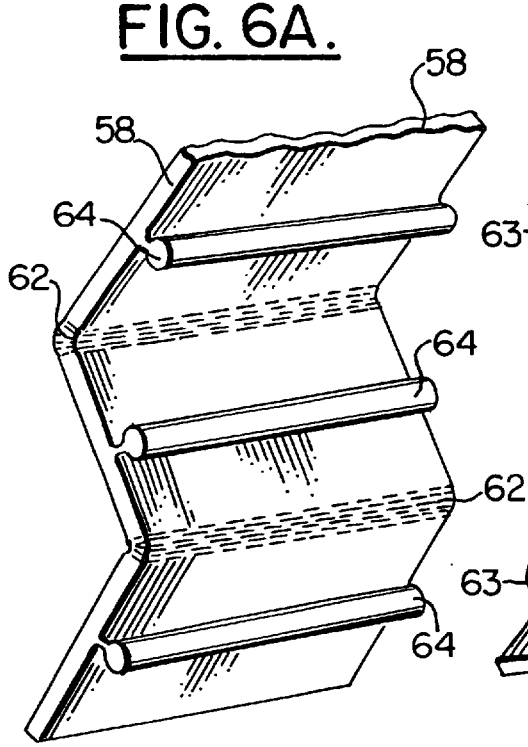
FIGS. 6A and 6B are fragmentary views of the preferred embodiment of the apparatus of the present invention showing an enlarged perspective view of individual segments of the shield.
Figure 6B:
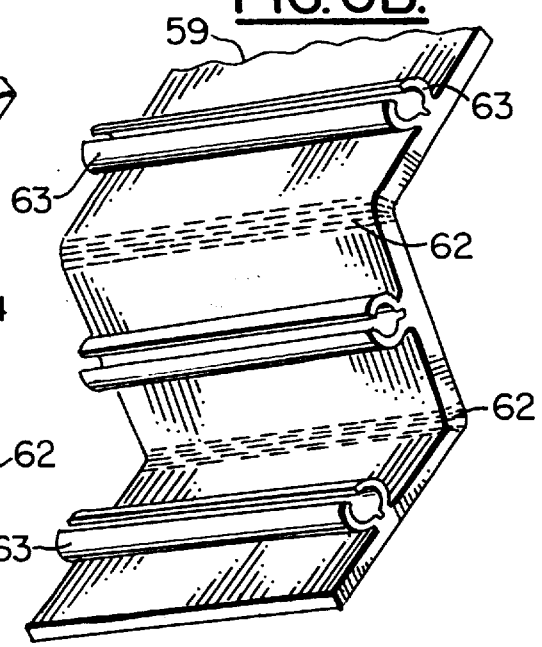

FIGS. 6a–6b illustrate in detail the projections 64 on half pieces 58, matching the slots 63 on half pieces 59. Also seen in detail is the flexible nature of hinges 62 joining horizontal shield segments 57.

It stands to reason that this construction of each of the lateral walls 56 of shield sections 52, 53 allows these shield sections to assume an infinite variety of positions. They can adapt to variations in the distance from camera 35 or radiation generator 36 to middle portion 47 by varying the degree of folding between horizontal shield segments 57 at hinges 62. They can adapt to variations in the size of the middle portion 47 by varying the degree of overlap 151 through increased or decreased engagement of half pieces 58 and 59. They can adapt to rotational movements and to angulated movements of the x-ray ensemble in relation to table 14 and middle portion 47, since the degree of folding between horizontal shield segments 57 can be different for each of the four lateral walls 56. This high degree of possible adaptation is illustrated in FIGS. 4a–4d.

Figure 7:
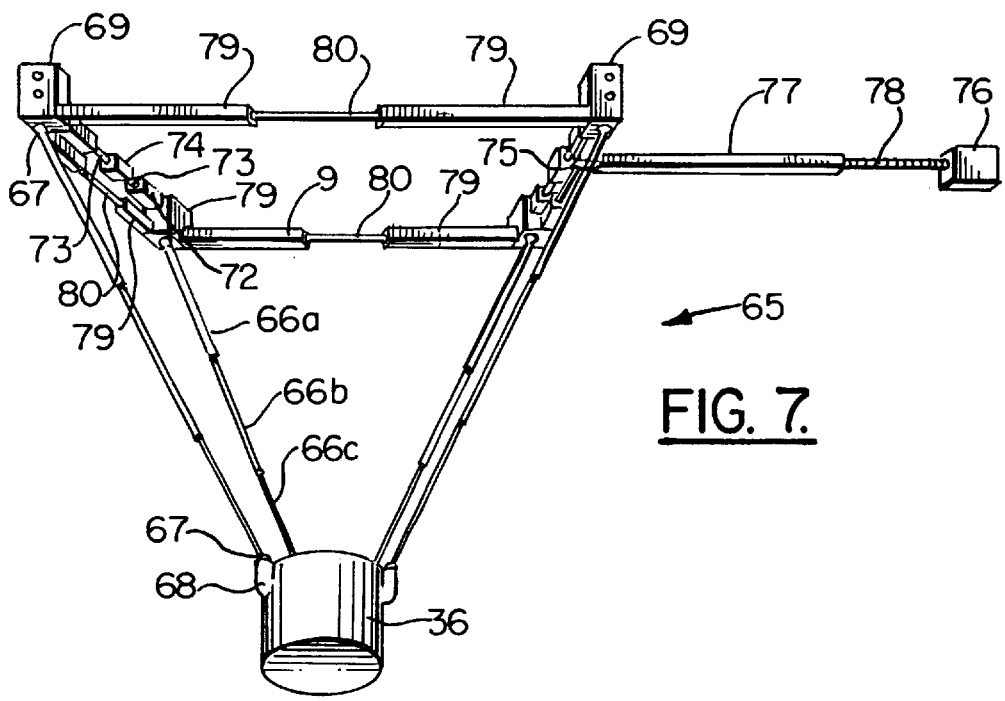
FIG. 7 is a fragmentary perspective view of the stabilizing rods of the lower shield, its frame at the base, and its connection to the drive unit.
Figure 8:
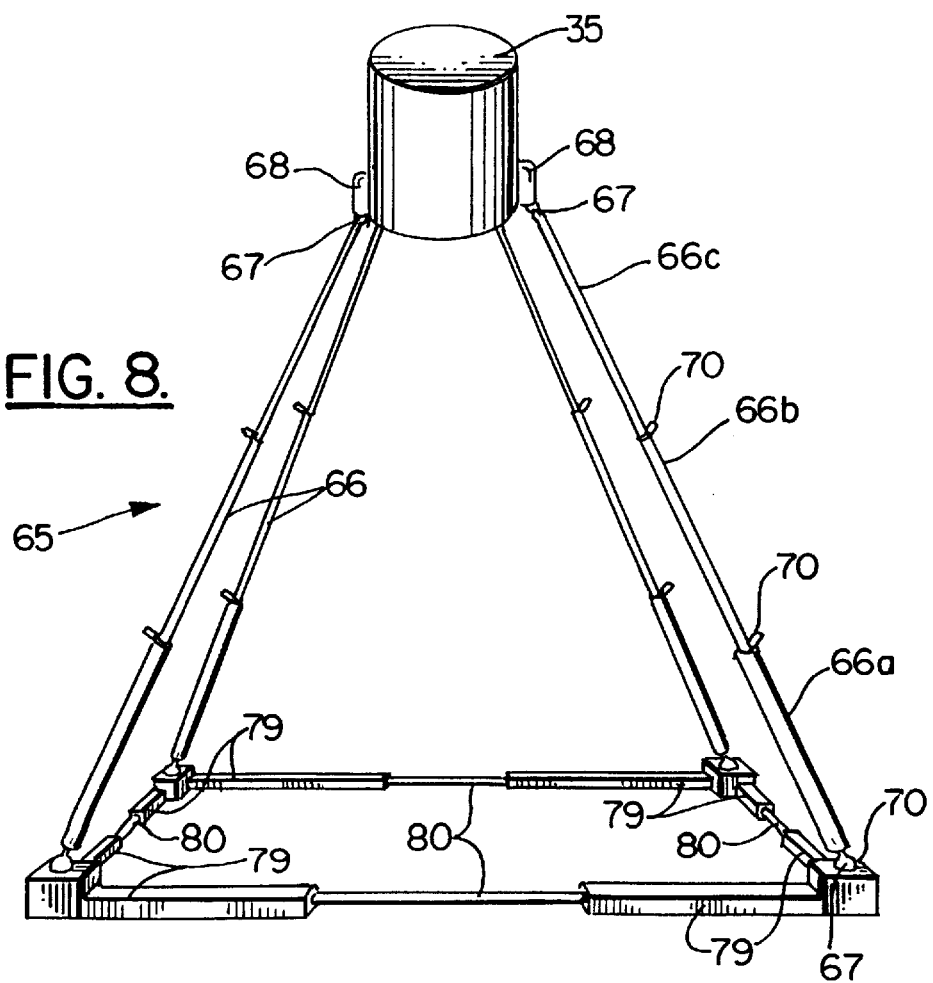
FIG. 8 is a fragmentary perspective view of the stabilizing rods of the upper shield, and its frame at the base.

In FIG. 7, frame 65 is shown that supports each bellows-like tapered shield sections 52 and 53. Each section 52, 53 is supported from the inside by frame 65 that includes stabilizing rods 66, consisting of three parts connected by a telescoping mechanism (66a, 66b, 66c), as illustrated in FIGS. 7 and 8. Ball joints 67 at the smaller end of these rods 66 fit into sockets 68 located at the radiation generator 36 and the camera 35 respectively. Ball joints 67 at the larger diameter ends of the rods 66 fit into sockets 68 located in connectors 69 and 70.

The connectors 69, 70 of a tapered section 52, 53 are connected to each other via shafts 79 and rods 80, whereby the rods 80 lead into tubular openings of the shafts 79 (not depicted), thus forming a telescoping connection (see FIG. 7). The telescoping mechanism of these supporting rods could be moved passively through the relative movement of table, radiation generator, and camera, or better through an internal hydraulic mechanism within the telescoping rods and shafts (not depicted), allowing for active extension or retraction of the three telescoping parts of the rods 66, synchronized with the movements of the ensemble of the X-ray apparatus, using computer guidance.

FIGS. 9A and 9B show the connection of tapered sections 52 and 53 to the frame 65 at rods 66. Connector rings 110 are located at each of the two telescoping joints linking the three parts 66a–66c of rods 66. FIG. 9A shows the structure of a connector ring 110. A large ring 110a is attached to the end of rod parts 66a and 66b at the point where the telescoping rod parts meet. Two radially extended struts 110b are attached with one end to the large ring 110a at an orthogonal angle to each other, and each strut has a smaller ring 110c at its other end. The rings 110c are in turn connected to metal loops 71 which are attached to the half pieces 58, 59 of a tapered section 52 or 53 by any conventional means. It should be noted that the size of the connectors shown in FIGS. 9A and 9B, and the distance from the rods to the shields, have been exaggerated for clarity.

At the end opposed to the radiation generator 36, the stabilizing rods 66 supporting the lower tapered section 53 are connected via ball joints 67 to connectors 69. These connectors form the corners of a drive unit located within the table board 14, which is depicted in detail in FIGS. 10 and 11.

In FIGS. 10–11, table board 14 consists of a base part 14b, and a cover part 14a. Attached to the connectors 69 are shafts 72 containing internal female threads into which thread rods 73 are connected. These threaded rods 73 are driven by small, reversible motors 74 and 75, which rotate the thread rods. Motor 74 is firmly attached to either the table base 14*b*, or the table cover 14*a*, whereas motor 75 is not attached to either. The two ends of threaded rods 73 emanating from the motors 74 and 75 have opposing helix directions, such that rotation of the threaded rods 73 in one direction will pull the attached shafts 72 and cubic connectors 69 towards the center of the table, whereas rotation in the opposite direction will push the attached shafts 72 and cubic connectors 69 away from the center of the table.

Motor 75 is also attached to an axial shaft 77, which contains an internal female threaded portion into which an axial threaded rod 78 connects. This threaded rod 78 is connected at one end to axial shaft 77, and at its other end to a third motor 76, which is attached firmly to the same portion of the table as motor 74. Rotation, by motor 76, of threaded rod 78 in one direction will pull the assembly of motor 75, threaded rods 73, shafts 72, and connectors 69 towards one end of the table, whereas rotation into the opposite direction will move these parts towards the opposite end of the table. The shafts 72 glide on conventional ball-bearings located in the two side openings 14*c* and 14*d* of the table base 14*b*. In addition, motors 74–76 can be connected to a source of electrical power via conventional electrical power cords 101.

FIGS. 12A and 12B show in detail the rod connections of a frame 65 that supports a tapered section 52, 53 and attachment to the drive unit. FIG. 12A shows a view of motor 74, connected via threaded rods 73 and shafts 72 to the connectors 69. Shafts 79 and rods 80 connect the four connectors 69 (only two of which are shown in FIG. 12A), thus forming a rectangle, as also depicted in FIG. 7. FIG. 12B shows a single connector 69, viewed from a different angle, with attached shafts 72 and 79 and rods 80.

FIG. 13A depicts the framework of the middle portion or rectangular housing 47 of shield 50. Angle struts 81 are connected via locking bolts 82 to holes 83 in the connectors 69 and 70. A conventional electric power lock mechanism allows for manual closure and central closure or release of the locking bolts 82.

FIGS. 14A–14C show different views of the upper and lower ends of angle struts 81, showing locking bolts 82 both in the locked and the released position. Side struts 84 (FIG. 13A) are attached to the angle struts 81 and lead into hollow bars 85, a portion of which is shown enlarged in FIG. 13B, each of which contain two parallel tracks 86 or apertures into which the side struts 84 connect. This allows the ends of the side struts 84 of the opposing angle struts 81 to move in adjacent, parallel tracks 86. The hollow bars 85 are attached to the upper and lower rims of plates 87 which contain a large rectangular opening 92. A row of conventional female snap-fasteners 88*a* are located around opening 92.

Hollow bars 89 are attached to the angle struts 81 in a direction orthogonal to the side struts 84. U-shaped bars 90 fit into the hollow bars 89. The connection of U-shaped bars 90 and hollow bars 89 is such that the ends of U-shaped bars 90 move freely within the hollow bars 89. A compression spring (not depicted) is located within each of the hollow bars 89, and this spring pushes U-shaped bars 90 away from angle struts 81. The length of these springs is such that U-shaped bars 90 and hollow bars 89 will not completely separate. Note that the vertical portion of each U-shaped bar 90 contains a row of conventional female snap-fasteners 88*a* similar to the snap fasteners 88*a* on elements 87.

Folding, X-ray impermeable screens 91, containing small, slit-like openings 111 located on the upper and lower ends of their folding segments 88 are attached to the middle, rectangular housing portion 47. Side struts 84, the hollow bars 89, and the horizontal portions of U-shaped bars 90 thread through the openings 111, as shown in FIGS. 15A–15C, thus allowing horizontal movements of the screens. The vertical ends of the screens are attached firmly to the vertical portion of the U-shaped bars 90, the vertical rims of angle struts 81, and the vertical rims of plates 87, by any conventional means. This ensemble is depicted in FIGS. 16A and 16B, and forms the side wing of middle portion 47.

Figure 17A:
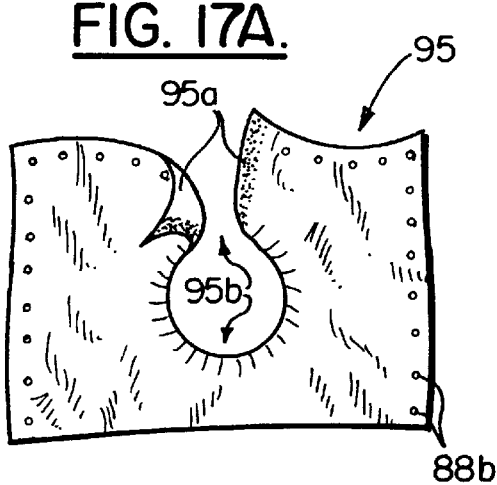
Figure 17B:
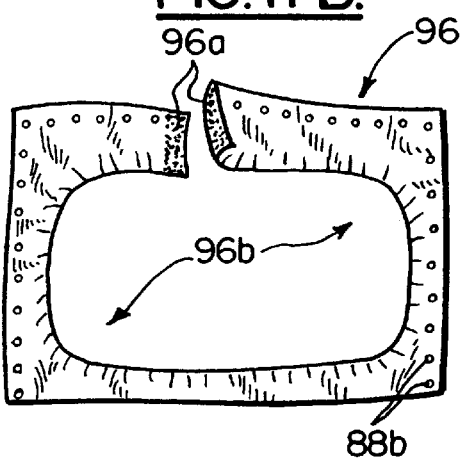
Figure 17C:
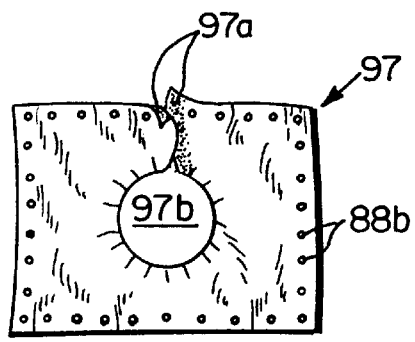
Figure 18:
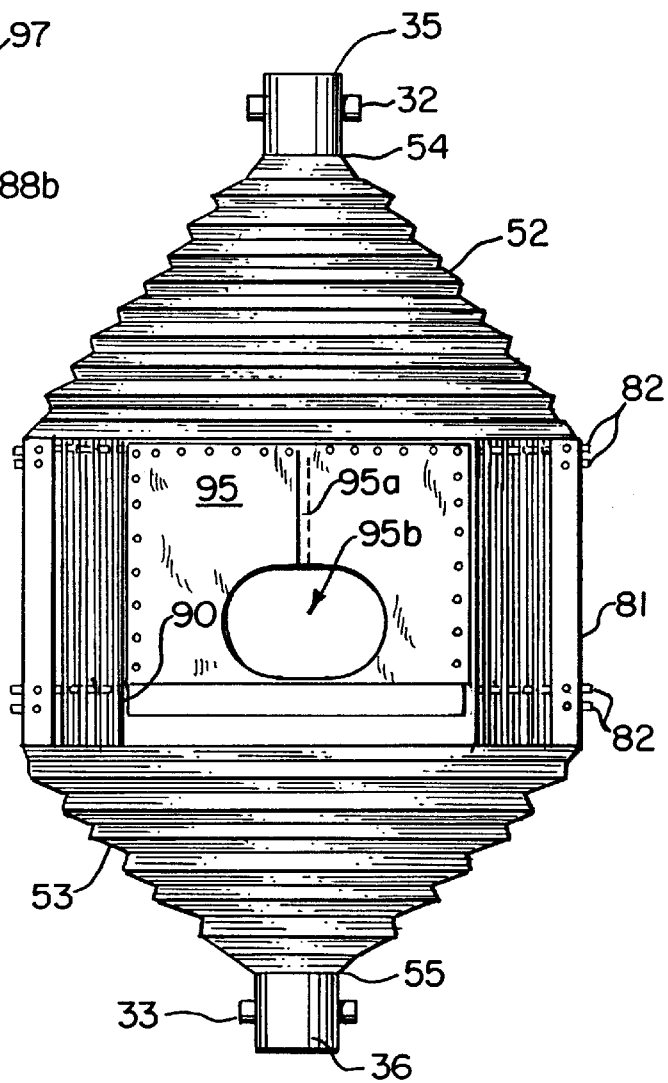
FIG. 18 is a top view of the present invention.

FIGS. 17A–17C depict "cuffscreens", which are rectangular pieces of flexible, stretchable, radio opaque material with an opening in the middle. These cuff screens can be opened and closed by means of VELCRO hook and loop type fasteners 95*a*, 96*a*, 97*a*, which lead from the openings 95*b*, 96*b*, 97*b* to the upper rim of the cuff screen. The cuff screens fit snugly around those parts of the patient's body that are leaving the middle housing portion 47 (see FIG. 3). Needed are one collar screen 95 for the patient's neck, one belt screen 96 for the waist, and two sleeve screens 97 for the arms. The outer rim of the cuff screens has a rim of male snap-fasteners 88*b*, which engage the female snap fasteners 88*a* on elements 81, 87, 90, to allow attachment to the framework of middle housing portion 47. FIG. 18 shows the middle housing portion 47, seen from the head 15 end of the table board 14.

FIGS. 19*a*, 19*b* and 20 show an armboard 98, which is hooked onto each of the two side wings of middle housing portion 47. These armboards 98 consist of a support rest 99, two rods 100 which slide into receiving tubes 109 within support rest 99 (thus allowing for adjustment of the armboards 98 to the varying distances between angle struts 81), and two side triangles 102, which attach via hooks 104 to sleeves 103 on angle struts 81 (see FIG. 13A).

FIG. 20 shows a horizontal cut of the key elements of the framework of middle portion 47 attached to the patient.

Figure 21A:
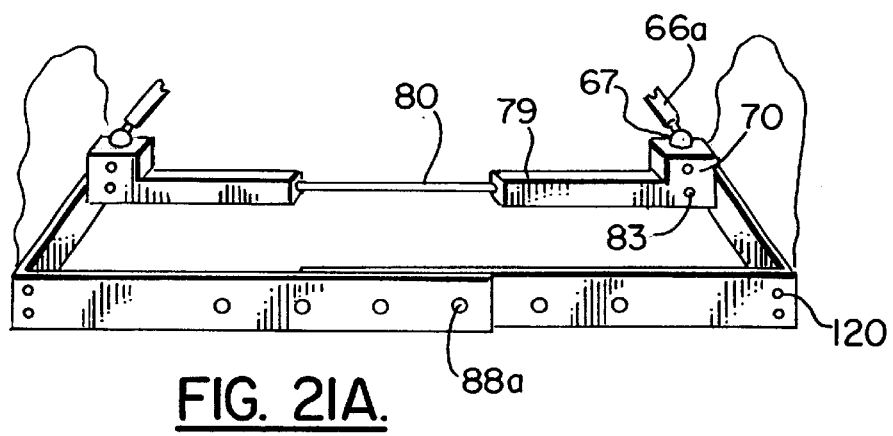
FIGS. 21A and 21B are perspective views of parts of the middle portion, the upper shield, and the frame of the upper shield of the present invention, separating the three structural groups of parts to illustrate their various positions.
Figure 21B:
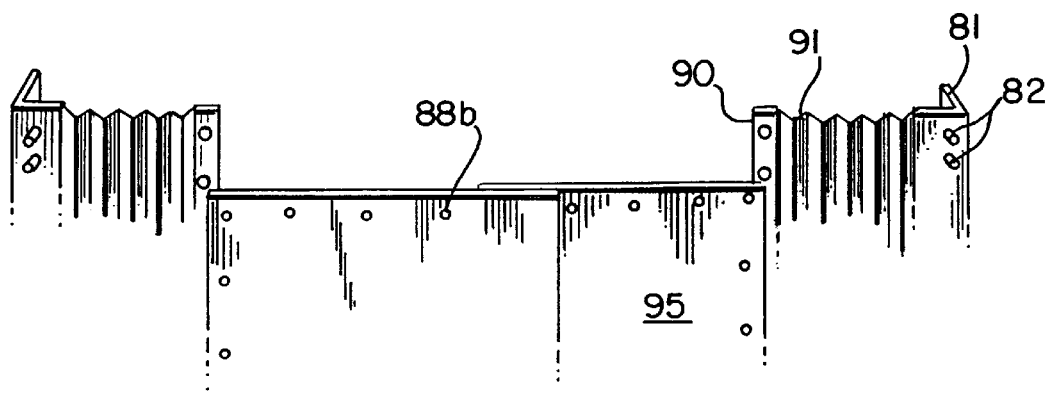

FIGS. 21A and 21B depict the connection between the upper tapered section 52 and the upper portion of middle housing portion 47. The lowermost segments of section 52 are attached to connectors 70. The upper ends of angle struts 81 are attached to connectors 70 by passing bolts 82 through holes 120 located in shield section 52, and then into holes 83 of connectors 70. One half of the lowermost segments of shield section 52 has a row of female snap fasteners 88*a*. Flexible collar screens 95 attach with male snap fasteners 88*b* to the female snap fasteners 88*a* located on the vertical portions of U-shaped bars 90 and the lowermost segments of shield section 52. Seen from the foot end of the table, the view would be similar, except that belt screen 96 would replace collar screen 95.

Figure 22:
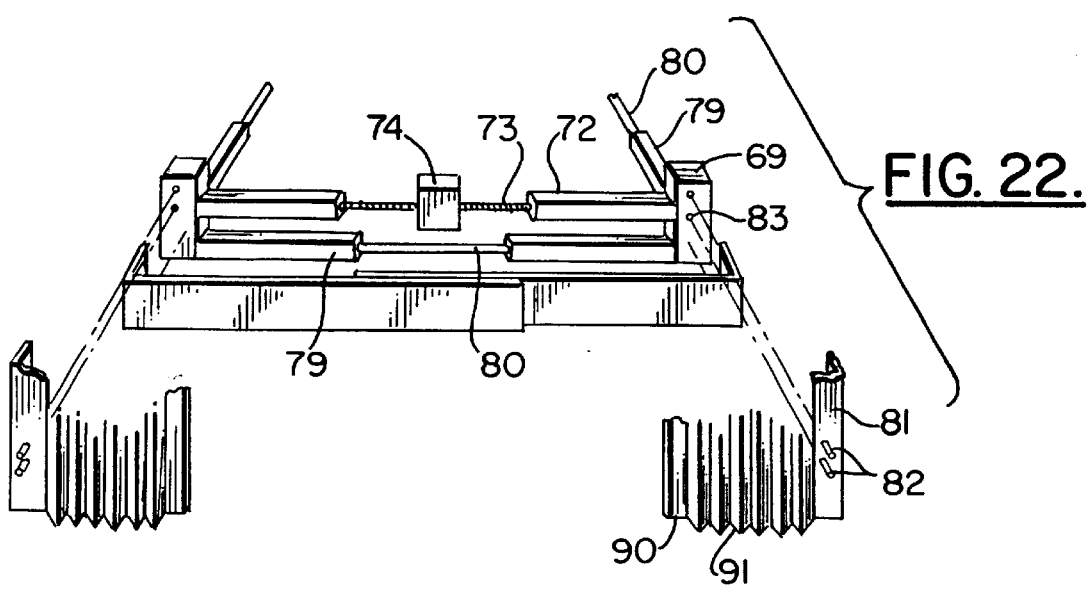
FIG. 22 is a perspective view of parts of the middle portion, the lower shield, the frame of the lower shield, and the drive unit, separating the parts similar to FIG. 21.

FIG. 22 depicts the connection between the upper portion of tapered section 53 and the lower portion of middle housing portion 47. The uppermost segments of tapered section 53 are attached firmly to the lower half of connectors 69. The lower ends of angle struts 81 are connected to the upper half of connectors 69 by inserting locking bolts 82 into holes 83.

FIG. 23 is a side view of the invention, showing the connection of the lower portion of shield 50 to radiation generator 36 via a special connection piece 93. Connection piece 93 is rectangular at its base, where it is firmly attached to the lowermost folding segment of tapered section 53. It is circular at its lower end, where it is firmly attached to the upper rim of radiation generator 36 at attachment, completely enclosing the connection of rods 66, ball joints 67, and joint sockets 68. A similar connection piece 94 is firmly attached with its rectangular base attachment 54 to the uppermost folding segment of tapered section 52, and with its circular end connected to the lower rim of camera 35, again covering the connection of parts 66, 67, 68. Both connection pieces 93 and 94 are made of radio impermeable material.

While many different variations of this design are possible to achieve the radiation shielding goals (the depicted design is only one of many different options), the unique new feature of this invention is the near complete isolation of the radiation space between the generator 36 and the camera 35 through a mobile shield that always adapts to the varying geometric relationships between the X-ray apparatus and the different organs in the patient's chest targeted for examination. The radiation beam 60 in its various positions in relation to the patient is always enclosed, allowing no scatter radiation 61 to escape.

An important point is that the material and structure of shield sections 52, 53 allow for asymmetry of the shields, which will occur as the X-ray apparatus moves, that it allow for a variation in the distance between radiation generator 36 and camera 35, and for a variation in the distance between either of these parts and table board 14.

The waist collar 96 has to be quite flexible, and the entire lower portion of this part has to be covered in sterile sheets, in order to allow the operator to move the region of vascular access into the radiation field for x-ray guidance, should this become necessary due to access problems.

The support structure of shield 50 has to be sufficient to allow the free passage of the radiation beam on its way from the radiation generator to the camera, without swinging of the shields into the trajectory of the X-ray beam when the shields assume angulated positions. This is achieved through the stabilizing rods 66 in this design, but other mechanisms can be used to achieve the same effect. The middle portion has been depicted as a simple assembly of a frame structure with folding screens and cuff screens with sleeve openings, but multiple variations of this design are also possible.

The present invention will allow open access to the patient's head, arms and groins. The only remaining leaks for scatter radiation are those parts of the patient's body which are emanating from the isolated radiation space. A telescoping mechanism located at camera 35 could be used to allow the camera to protrude to varying degrees directly into the shielded space formed by tapered section 52.

Several other features are important. The device of the present invention can be disassembled very quickly, so that effective cardiopulmonary resuscitation can be rendered without delay in the case of cardiac arrest. Sensitive radiation detection devices have to be installed outside the confinements of the radiation field isolator, in order to prevent accidental exposure of the operators to scatter radiation leaks. While the device presented is intended for diagnostic and therapeutic procedures using radiation for imaging purposes, minor modifications in the design would easily allow to use this device for radiation therapy.

Although the Radiation Field Isolator and the method of using the same according to the present invention have been described in the foregoing specification with considerable details, it is to be understood that modifications may be made to the invention which do not exceed the scope of the appended claims, and modified forms of the present invention done by others skilled in the art to which the invention pertains will be considered infringements of this invention when those modified forms fall within the claimed scope of this invention.

The following is a list of parts and materials suitable for use in the present invention:

PARTS LIST

| Part Number | Description |
| --- | --- |
| 10 | shielded x-ray apparatus |
| 11 | frame |
| 12 | lower end portion |
| 13 | upper end portion |
| 14 | table |
| 14a | cover part |
| 14b | base part |
| 14c | opening |
| 14d | opening |
| 15 | head end |
| 16 | foot end |
| 17 | upper surface |
| 18 | patient |
| 19 | attachment |
| 20 | x-ray unit |
| 21 | base |
| 22 | vertical section |
| 23 | horizontal section |
| 24 | pinned connection |
| 25 | support beam |
| 26 | superstructure |
| 27 | pinned connection |
| 28 | pinned connection |
| 29 | arrow |
| 30 | arm |
| 31 | arm |
| 32 | upper yoke |
| 33 | lower yoke |
| 34 | arrow |
| 35 | camera |
| 36 | radiation generator |
| 37 | beam |
| 38 | beam |
| 39 | monitor |
| 40 | monitor |
| 41 | monitor support |
| 42 | reference line |
| 43 | arrow |
| 44 | arrow |
| 45 | pinned connection |
| 46 | pinned connection |
| 47 | rectangular housing or middle portion |
| 48 | wall |
| 49 | flexible panel |
| 50 | shield |
| 51 | opening |
| 52 | upper tapered section |
| 53 | lower tapered section |
| 54 | upper attachment |
| 55 | lower attachment |
| 56 | flexible lateral wall |
| 57 | horizontal shield segments |
| 58 | half piece |
| 59 | half piece |
| 60 | radiation beam |
| 61 | scatter radiation |
| 62 | hinge |
| 63 | slotted receptacle |
| 64 | projecting member |
| 65 | frame |
| 66 | rod |
| 66a | telescoping part |
| 66b | telescoping part |
| 66c | telescoping part |
| 67 | ball joint |
| 68 | socket |
| 69 | connector |
| 70 | connector |
| 71 | loop |
| 72 | shaft |
| 73 | threaded rod |
| 74 | reversible motor |

-continued

PARTS LIST

| Part Number | Description |
| --- | --- |
| 75 | reversible motor |
| 76 | reversible motor |
| 77 | axial shaft |
| 78 | threaded rod |
| 79 | shaft |
| 80 | rod |
| 81 | angle strut |
| 82 | locking bolt |
| 83 | hole |
| 84 | side strut |
| 85 | bar |
| 86 | parallel tracks |
| 87 | plate |
| 88 | folding segment |
| 88a | female snap fastener |
| 88b | male snap fastener |
| 89 | bar |
| 90 | bar |
| 91 | screen |
| 92 | opening |
| 93 | connecting piece |
| 94 | connecting piece |
| 95 | collar screen |
| 95a | VELCRO fastener of collar screen |
| 96 | belt screen |
| 96a | VELCRO fastener of belt screen |
| 96b | opening of belt screen |
| 97 | sleeve screen |
| 97a | VELCRO fastener of sleeve screen |
| 97b | opening of sleeve screen |
| 98 | armboard |
| 99 | support rest |
| 100 | rod |
| 101 | power cord |
| 102 | side triangle |
| 103 | sleeves |
| 104 | hooks |
| 109 | receiving tubes |
| 110 | connector ring |
| 110a | ring |
| 110b | strut |
| 110c | small ring |
| 111 | slit like opening |
| 120 | hole |
| 151 | section of overlap |

The forgoing embodiments are presented by way of example only; the scope of the present invention to be limited only by the following claims.

What is claimed is:

1. An isolation system to be used with radiation equipment for protecting operating personnel from stray radiation, said radiation equipment comprising:
   a) a source of radiation;
   b) a shield that comprises:
      a middle shielding section having an interior for holding all or part of a patient's body;
      a second shielding section attached to said middle section and to the radiation source; and
   c) wherein the shield forms an envelope about an area in between the radiation source and the patient.

2. The isolation system of claim 1 further comprising a camera and a third shielding section attached to the middle section and the camera.

3. The isolation system of claim 2 wherein the camera and radiation source are generally opposite each other on opposing sides of said middle section.

4. The isolation system of claim 2 wherein one of said second and third sections is tapered.

5. The isolation system of claim 2 wherein both of said second and third sections is tapered.

6. The isolation system of claim 2 wherein one of said second and third sections have a flexible wall.

7. The isolation system of claim 2 wherein both of said second and third sections has a flexible wall.

8. The isolation system of claim 2 wherein one of said second and third sections is in the form of a bellows like structure having folded wall portions.

9. The isolation system of claim 2 wherein both of said second and third sections are in the form of a bellows like structure having folded wall portions.

10. The isolation system as claimed in claim 5, wherein each of said tapered sections comprises four trapezoid side surfaces,
    each trapezoid surface consisting of two overlapping sections,
    each section consisting of a plurality of segments movably connected together,
    said segments being connected together by flexible material,
    said overlapping sections being slidably connected to each other.

11. The isolation system as claimed in claim 2, wherein each of said shield sections is supported by a plurality of stabilizing rods,
    each of said stabilizing rods comprising a plurality of telescoping rod sections,
    said stabilizing rods supporting said second shield section having means at one end for connecting said stabilizing rods to said radiation source, and means at another end for connecting said stabilizing rods to said middle section,
    said stabilizing rods supporting said third shield section having connectors at one end for connecting said stabilizing rods to said camera, and connectors at another end for connecting said stabilizing rods to said middle shielding section.

12. The isolation system of claim 11 wherein the connectors include a plurality of connector rings.

13. The isolation system of claim 12 wherein each one of said connector rings has at least two loops, one of said at least two loops being connected to one of said stabilizing rods, and another of said at least two loops being connected to said shield sections.

14. The isolation system as claimed in claim 1, wherein said middle shielding section comprises two side sections,
    each of said side sections comprising a middle piece and two end pieces,
    each of said middle pieces comprising a rectangular plate, each having a rectangular opening and a lower and an upper end,
    each of said lower and upper ends of said rectangular plates being connected to a horizontal bar,
    each of said horizontal bars having two parallel slots extending there through.

15. The isolation system as claimed in claim 14, wherein each of the end pieces of said side sections comprise a vertical support having a fist corner piece connected to a second corner piece,
    said first and second corner pieces being connected together at an angle,
    a pair of horizontal bars extending from each of said corner pieces,
    said pair of horizontal bars extending from said first corner piece engaging said slots in said horizontal bars on said middle piece, said pair of horizontal bars extending from said second corner piece engaging a U-shaped bar, said U-shaped bar having a vertical leg and two horizontal legs.

16. The isolation system as claimed in claim 15, wherein said pair of horizontal bars extending from said second corner piece are hollow, and have a spring positioned within said hollow space, said horizontal legs on said U-shaped bar entering said hollow horizontal bars and engage said spring.

17. The isolation system as claimed in claim 6, wherein flexible walls have a central aperture therein are located between and attached to said vertical legs of said U-shaped bars, said flexible walls extending across said table, said central apertures of said flexible screens having a slot extending to a periphery of said flexible screens, and means for closing said slot.

18. The isolation system of claim 1 further comprising a table that supports said middle section.

19. The isolation system of claim 18 further comprising a camera and a third shielding section attached to the middle section and the camera.

20. The isolation system of claim 18 wherein the camera and radiation generator are generally opposite each other on opposing sides of said middle section.

21. The isolation system of claim 18 wherein one of said second and third sections is tapered.

22. The isolation system of claim 18 wherein both of said second and third sections is tapered.

23. The isolation system of claim 18 wherein one of said second and third sections has a flexible wall.

24. The isolation system of claim 18 wherein both of said second and third sections has a flexible wall.

25. The isolation system of claim 18 wherein one of said second and third sections is in the form of a bellows like structure having folded wall portions.

26. The isolation system of claim 18 wherein one of said second and third sections is in the form of a bellows like structure having folded wall portions.

27. An isolation system to be used with radiation equipment for protecting operating personnel from stray radiation, said radiation equipment comprising:

a) frame that includes a table for supporting a patient;
b) a source of radiation;
c) a camera positioned to receive radiation that has passed through the patient;
d) a shield that comprises:
   i a middle shielding section having an interior for holding all or part of a patient's body;
   ii a second shield section attached to said middle section and the radiation generator;
   iii a third shield section attached to said middle section and the camera;
e) wherein the shield forms an envelope about an area in between the radiation source and the camera.

* * * * *